United States Patent [19]

Goble et al.

[11] Patent Number: 4,901,711
[45] Date of Patent: Feb. 20, 1990

[54] DRILL GUIDE

[76] Inventors: E. Marlowe Goble, 850 E. 1200 North; W. Karl Somers, 651 N. 150 West, both of Logan, Utah 84321

[21] Appl. No.: 290,423

[22] Filed: Dec. 27, 1988

[51] Int. Cl.⁴ .............................................. A61F 5/04
[52] U.S. Cl. ........................................ 606/98; 606/97
[58] Field of Search ......... 128/92 V, 92 VD, 92 VW, 128/92 VL, 92 VZ, 92 Y, 92 YF, 92 YC, 92 YJ, 92 YD, 92 Z

[56] References Cited

U.S. PATENT DOCUMENTS

| | | | |
|---|---|---|---|
| 2,267,157 | 12/1941 | Lippincott | 128/92 VD |
| 4,257,411 | 3/1981 | Cho | 128/92 VD |
| 4,535,768 | 8/1985 | Hourahane et al. | 128/305.1 |
| 4,573,459 | 3/1986 | Litton | 128/92 Z |
| 4,722,331 | 2/1988 | Fox | 128/92 VD |
| 4,773,417 | 9/1988 | Moore et al. | |
| 4,781,182 | 11/1988 | Purnell et al. | |
| 4,784,126 | 11/1988 | Hourahane | |
| 4,787,377 | 11/1988 | Laboureau | |

OTHER PUBLICATIONS

Johnson & Johnson, "The AI Guide: Arthroscopic, Isometric ACL Reconstruction", Jan. 1988.

Primary Examiner—Robert A. Hafer
Assistant Examiner—Lynda M. Cofsky
Attorney, Agent, or Firm—M. Reid Russell

[57] ABSTRACT

The present invention is in a drill guide (20) that is for use with and for mounting to a "K" wire (13) that has been fitted through an anterior or posterior cruciate ligament tunnel. The drill guide (20) includes identical parallel rails (21) that are mounted to a stationary bracket (22), essentially at right angles, and are journaled to a traveling bracket (25), the traveling bracket further including set screws (28) to releasably lock it to the rails. The stationary and traveling brackets (22) and (25), respectively, are each isosceles triangular in shape, and each mounts a guide cylinder (23) and (26), respectively, at right angles through their apexes such that longitudinal openings through which guide cylinders are aligned to receive the "K" wire fitted therethrough. A trolley (30) is arranged for travel on rails (21) between the stationary and traveling brackets (22) and (25), and can be releasably locked in place. The trolley mounts a replaceable drill sleeve (36) with a barrel (40) that includes a longitudinal hole (41) formed therethrough wherethrough a drill (44) is turned.

9 Claims, 2 Drawing Sheets

DRILL GUIDE

BACKGROUND OF THE INVENTION

1. Field of the Invention

The invention relates to surgical devices and in particular to devices for use in knee reconstructive surgery that enables a surgeon to form a tunnel through the side of a patient's knee to exactly intersect an anterior or posterior cruciate ligament tunnel that has been formed through the knee.

2. Prior Art

In cruciate ligament repair and replacement surgery it is common to drill tibial and femoral tunnel sections as the ligament tunnel through the respective femoral and tibial points of ligament origin. Such tunnels can be formed as shown in patents and a new patent application, respectively, of the present inventors, entitled, "Ligament Attachment Method and Apparatus", U.S. Pat. No. 4,772,286; and "Apparatus and Procedure for Verifying Isometric Ligament Positioning". The ligament tunnel is to receive a biologic or prosthetic ligament installed therein, the installed ligament to be maintained in a tension state across the intra articular knee joint during healing. The present invention in a drill guide is arranged to reference a straight "K" wire to receive the present invention fitted thereover.

The present invention in a drill guide is for use for guiding the drilling of a hole into the side of the femur or tibia so as to intersect the cruciate ligament tunnel. So prepared, a coupling device, such as a screw can be turned into the side of a ligament end coupling that has been turned into a tapped end of the prepared ligament tunnel section, or into the ligament itself, providing an increased pull out strength to that ligament.

A number of drill guide arrangements have heretofore been developed for forming cruciate ligament tunnels. For example, patents to Sapeya, et al., U.S. Pat. No. 4,739,751; Cho, U.S. Pat. No. 4,257,411; Hourahane, et al., U.S. Pat. No. 4,535,768; Hourahane, U.S. Pat. No. 4,672,957; and a United Kingdom Patent to Lovell, et al., No. 2,078,528, all show arrangements for drilling cruciate ligament tunnel sections through the intra articular joint from a point on the tibial or femoral cortex to intersect the end of a guide that is positioned on a cruciate ligament point of origin. Also, patents to Seedholm, et al., U.S. Pat. No. 4,668,233, and a European Patent Application 0126529, show a prosthetic ligament and drill guide for preparing tibial and femoral tunnel sections.

None of which above-cited references, however, are structurally like the drill guide of the present invention, and, further, none provide for drilling a right angle tunnel so as to exactly intersect a tibial or femoral cruciate ligament tunnel section as does the present invention.

SUMMARY OF THE INVENTION

It is a principal object of the present invention in a drill guide to provide an arrangement for enabling a surgeon, performing a cruciate ligament replacement surgical procedure, to drill a hole or tunnel from without the knee so as to intersect, at approximately a right angle, a desired point in a cruciate ligament tunnel that has been formed through the intra articular joint.

Another object of the present invention is to provide a drill guide for use in a surgical procedure for guiding from the side, a drill that is turned into a patient's knee, to intersect, at a right angle, a specific point of location along a prepared cruciate ligament tunnel.

Still another object of the present invention is to provide a drill guide that references a straight "K" wire, or the like, that has been installed through aligned cruciate ligament tunnel sections, to enable a surgeon, from any point around the knee, from one side of the leg to the other, to easily and accurately drill a lateral hole or tunnel so as to exactly intersect a point along the aligned cruciate ligament tunnel sections.

The present invention is in a drill guide that is intended for use in a knee surgical procedure where a cruciate ligament tunnel has been formed through the knee, exiting both the femoral and tibial cortexes. The drill guide of the present invention is for mounting to a "K" wire, or the like, that has been fitted through the ligament tunnel or tunnel sections to guide a surgeon drilling a lateral passage or tunnel from a point that is without the knee. Which drill can be from any point around an arc from one side of the leg knee area to the other, to exactly intersect, at essentially a right angle, the cruciate ligament tunnel. The drill guide is arranged for installation onto the ends of a "K" wire that has been passed through the cruciate ligament tunnel, exiting both the femoral and tibial cortexes.

The drill guide fits the "K" wire through aligned guide cylinders and may include a sleeve for telescoping therein to receive the "K" wire passed therethrough to provide a close fit that allows for axial rotation of the drill guide on that "K" wire. The guide cylinders are mounted on brackets, spaced apart on parallel rails, one of which brackets is arranged to slide along the parallel rails, and can be removed therefrom for mounting the "K" wire. A trolley of the drill guide is arranged to travel along the rails, between the brackets. The trolley includes a body that is arranged to receive a removable drill sleeve for replaceable mounting thereto, that extends at a right or normal angle to the rails. Which cylindrical drill sleeve is open therethrough to "point" at the "K" wire. The trolley can be positioned at any point along the rails and includes, as does the traveling bracket, a friction locking arrangement for releasably holding it in place. Preferably the cylindrical drill sleeve is removable by turning it into and out of the trolley body for accommodating different diameters of barrels over a range of drill sizes for fitting therethrough.

BRIEF DESCRIPTION OF THE DRAWINGS

These and other objects and features of the present invention in a drill guide will become more fully apparent from the following description in which the invention is described in detail in conjunction with the accompanying drawings.

DETAILED DESCRIPTION

Figure 1:
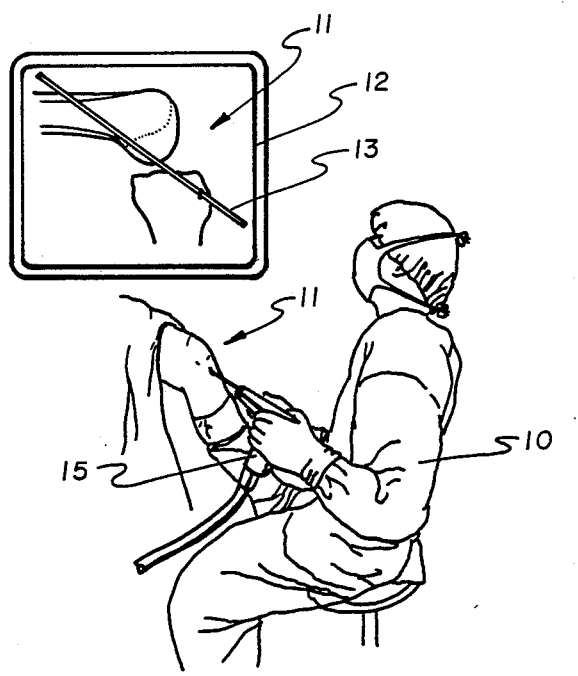
FIG. 1 shows a surgeon seated before a patient's flexed knee observing a fluoroscopic monitor and drilling, from the tibial tuberosity, an anterior cruciate ligament tunnel, the drill passed through the intra articular joint and both the cruciate ligament points of origin and the tibial and femoral cortexes.

FIG. 1 shows a surgeon 10 seated in front of a patient's knee 11 practicing an arthroscopic surgical procedure for replacing the patient's anterior cruciate ligament with an allograft or prosthetic ligament. In the procedure, the surgeon observes, on a fluoroscopic monitor 12, the passage of a drill turned by a driver 15 through the tibial tuberosity into the knee 11 intra articular joint, passing through both the femoral and tibial points of ligament attachment or origin, and the drill shown as having exited the femur anterolateral cortex. So arranged, with the driver 15 removed and with a "K" wire 13, fitted through knee 11, the "K" wire ends will extend beyond the tibial tuberosity and femoral anterolateral cortex. A drill guide 20 of the present invention can then be fitted thereover, as illustrated in FIG. 2.

Figure 2:
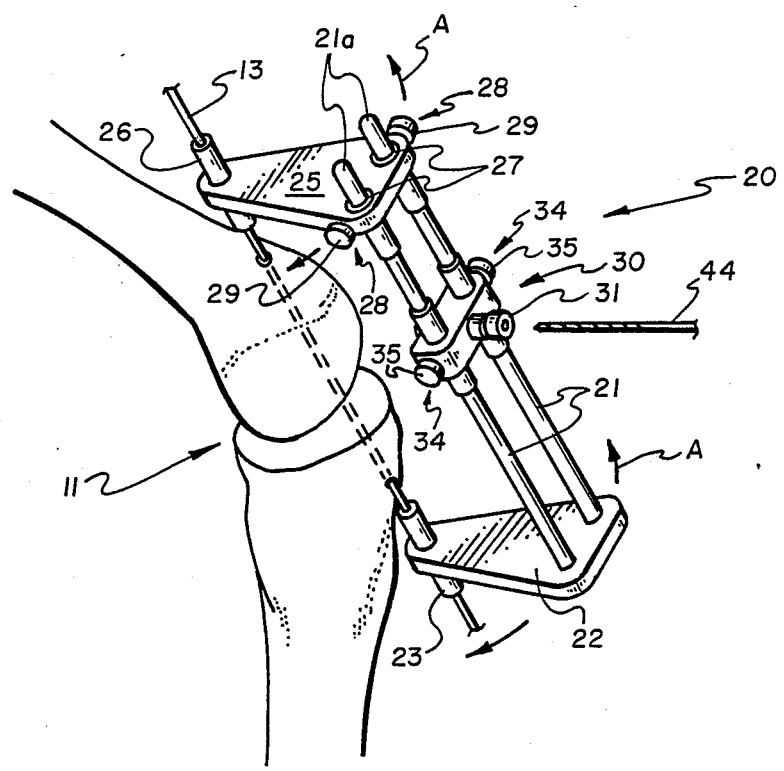
FIG. 2 shows a slide elevation view perspective of a "K" wire installed in the ligament tunnel of FIG. 1 with aligned guide cylinders of brackets of the drill guide of the present invention shown telescoped thereover, the brackets shown mounted on parallel rails with a trolley shown mounted to travel along the parallel rails, and showing a drill aligned for fitting through a drill sleeve barrel that is aligned at approximately a right angle to the "K" wire.
Figure 3:
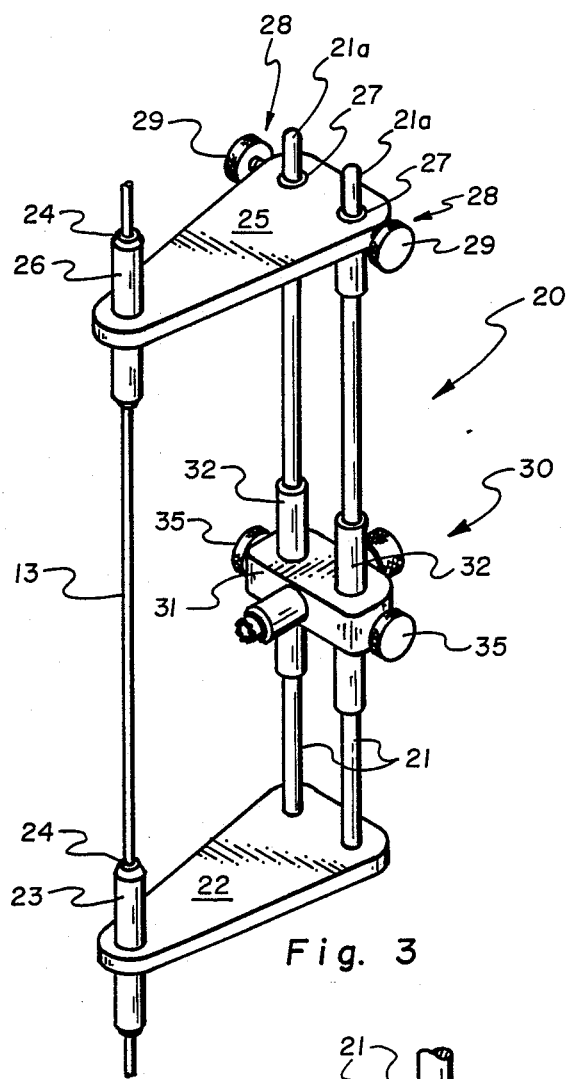
FIG. 3 shows a side elevation perspective view of the drill guide and "K" wire of FIG. 2 removed from the knee.

FIGS. 2 and 3 show the drill guide 20 as preferably consisting of a pair of identical spaced apart parallel rails 21. Each rail 21 is fixed at its one end to one of two base corners of a stationary isosceles triangular shaped bracket 22, hereinafter referred to as stationary bracket. The stationary bracket at its apex, includes an guide cylinder 23 that is open longitudinally, is secured to extend at a right angle therethrough, and is parallel to the rails 21.

The opposite rail 21 ends are preferably rounded at 21a and receive a traveling isosceles triangular shaped bracket 25, hereinafter referred to as traveling bracket, journaled thereover. The traveling bracket 25 also includes an open guide cylinder that, like guide cylinder 23, is open longitudinally and is secured through the traveling brackets apex, such that the longitudinal openings through the respective open guide cylinders 23 and 26 are to align with each other to accommodate the "K" wire 13 fitted therethrough. Where the longitudinal opening through the guide sleeves is of a greater diameter than the "K" wire, as shown best in FIG. 3, sleeves 24, can be installed on the guide cylinders longitudinal passages to provide a close fit to the "K" wire while still allowing the drill guide to rotate freely thereon.

The traveling bracket 25 is holed at 27, proximate to each of the triangle base corners, to accommodate rail rounded ends 21a fitted therethrough. Set screws 28 are provided for locking the traveling bracket 25 in place on the rails 21. The set screws 28 are turned into threaded lateral holes that are formed from the hypotenuse sides of that traveling bracket, proximate to their junctions with the base, to intersect holes 27. Shown in FIGS. 2 and 3, the set screws 28 include both threaded shafts for turning into the laterally threaded holes, and enlarged head ends 29 that are to be manually turned. So arranged, by turning the set screw 28 end out of engagement with the rails 21, the traveling bracket 25 is released and can be slid therefrom. This allows the guide cylinder 26 to be slid off from or fitted over a "K" wire 13 end. This arrangement provides for mounting the drill guide 20 to the "K" wire 13, as shown best in FIG. 2.

Figure 4:
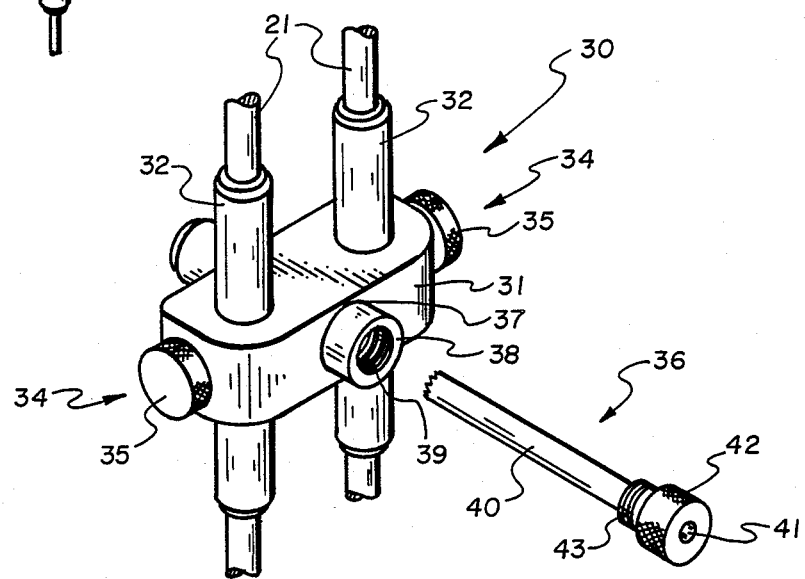
FIG. 4 shows an enlarged view of the trolley of FIG. 3 arranged on sections of the drill guide rails and shows the drill sleeve exploded therefrom.

Shown in FIGS. 2, 3 and 4, the rails 21 serve also as guides for supporting travel of a trolley 30 therealong. Trolley 30 is shown to consist of a rectangular slide body 31 that is holed through and between opposite parallel top and bottom faces as shown best in FIG. 4 to pass rail sleeves 32 fitted therethrough that accommodate the support rails 21 journaled therethrough. The slide body 31 is also holed and tapped at opposite ends, each hole to receive a locking screw 34 turned therein. Each of which locking screws 34 includes a broad head end 35 that is for manual turning to move a screw end thereof, not shown, into engagement with the side of a rail sleeve 32. Each locking screw 34 is used to lock the trolley 30 to a rail 21. In practice, each rail sleeve 32 may be holed opposite to the end of locking screw 34, such that the locking screw end will pass through the rail sleeve and engage the side of rail 21. Within the scope of the disclosure, the rail sleeve 32 may be a linear bearing that is holed to accommodate the locking screw end traveling therethrough. Or, the rail sleeve 32 may be splint longitudinally, the locking screw end to butt thereagainst so as to cause that rail sleeve to flex into engagement with the side of rail 21.

Arranged as set out above, the trolley 30 is free to move along and lock to rails 21, between the stationary and traveling brackets, 22 and 25, respectively. The trolley function, as shown in FIG. 2, is to align and guide a drill 44 for turning through a drill sleeve 36 that is mounted to the trolley. Shown best in FIG. 4, the drill sleeve 36 is fitted through a support tube 38 that is mounted through a lateral hole 37 formed through the trolley slide body 31. The open support tube 38 includes internal threads 39 that are formed in one end to accommodate threads 43 of a collar of a barrel 40 portion of drill sleeve 36 turned therein. The drill sleeve is shown to include a longitudinal hole 41 that is formed therethrough as a barrel, and has a head end 42 for manual turning. The drill sleeve barrel longitudinal hole has a diameter to accommodate a certain size of drill 44. The threaded collar 43 is arranged adjacent to the drill sleeve head end 42 for turning in the support tube internal threads 39. So arranged, the drill sleeve 36 is easily mounted to and demounted from the trolley 30. The longitudinal hole 41 of the drill sleeve functions as a barrel to exactly point at the "K" wire 13 and drill sleeve 36 having different diameters of longitudinal holes 41 and accommodates different sizes of drills 44 turned into the knee at any position of trolley 30 along rails 21 and around the knee.

FIG. 2 shows the drill guide 20 of the present invention mounted to the "K" wire 13 with a drill 44 shown aligned for turning through the longitudinal hole 41 of the drill sleeve 36. Which drill 44 is for turning into the distal femur or proximal tibia to exactly intersect, at essentially a right angle, the anterior cruciate ligament tunnel, as shown in FIG. 1.

Figure 5:
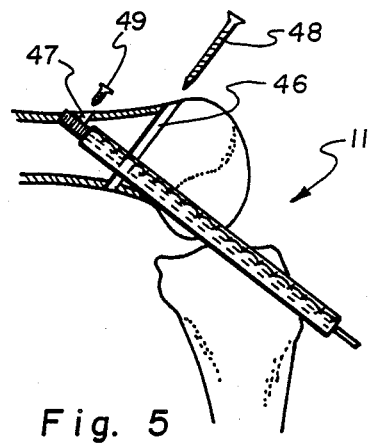
FIG. 5 shows an allograft anterior cruciate ligament fitted into the prepared tunnel with right angle holes shown intersecting that tunnel and showing screws aligned for turning therein.

FIG. 5 shows the patient's knee 11 with the anterior cruciate ligament tunnel having been enlarged and the femoral anterolateral cortex tapped for securing a ligament in one tunnel end. A threaded cylinder 45 is shown secured to an end of the allograft ligament and is for turning into the threads of the tapped femoral anterolateral cortex. Prior to that allograft ligament installation the distal demur is shown as having been drilled, utilizing the drill guide 20, as described above, forming holes 46 and 47. Hole 46 is shown as having passed through opposite femur cortexes, and the hole 47 is shown to intersect the ligament tunnel, adjacent to the tapped cortex. Fasteners, shown as long and short screws 48 and 49, respectively, are aligned with holes 46 and 47, respectively. The long screw is to turn through the ligament and both cortexes, thereby purchasing two cortexes to greatly increase the ligament pull-out strength. The short screw 49 is shown aligned to turned into the threaded cylinder 45, functioning as a set screw, to maintain ligament positioning and increase pull-out strength.

As illustrated by curved arrows A in FIG. 2, the drill guide 20 can be rotated in an arc around the knee 11, from one side of the knee to the other. So arranged, holes or tunnels can be formed from any number of points without the distal femur and proximal tibia to exactly intersect the ligament tunnel.

Where the drill guide 20 has been shown and described with respect to a surgical procedure involving replacement of an anterior cruciate ligament it should, of course, be apparent that the invention can be used equally well in a posterior cruciate ligament replacement procedure. Further, it should be understood, the drill guide 20 can even be used in other procedures where both ends of a "K" wire, or the like, are available for mounting and referencing the drill guide for use in drilling a passage or tunnel that will intersect such "K" wire, or the like, within the scope of this disclosure.

While a preferred embodiment of the present invention in a drill guide and its use have been shown and described herein, it should be apparent that this disclosure is made by way of example only and that variations and modifications to the apparatus and its use are possible within the scope of this disclosure without departing form the subject matter coming within the scope of the following claims, and a reasonable equivalency thereof, which claims we regard as our invention.

We claim:

1. A drill guide comprising, a pair of parallel rails; a stationary bracket mounted to spaced apart aligned ends of said parallel rails, which stationary bracket includes a first longitudinally open guide cylinder that extends therefrom, parallel to said parallel rails; a traveling bracket journaled to said parallel rails other ends to travel therealong, which traveling bracket includes a second longitudinally open guide cylinder that extends therefrom, parallel to said rails; trolley means journaled for travel along said rails; and drill sleeve means for mounting to said trolley, said drill sleeve means having a barrel portion that is open therethrough that will align with a straight wire or pin that is installed through said first and second longitudinally open guide cylinders.

2. A drill guide as recited in claim 1, wherein the identical parallel rails are solid rods; and the stationary and traveling brackets are identical flat isosceles triangles, with said parallel rails each installed in the brackets proximate to each of the base corners of each said stationary and traveling bracket.

3. A drill guide as recited in claim 2, wherein the first and second guide cylinders are installed at right angles through the apex of each of the stationary and traveling brackets.

4. A drill guide as recited in claim 1, further including means for locking the traveling bracket to at least one of the parallel rails.

5. A drill guide as recited in claim 4, wherein the means for locking is at least one set screw means arranged for manual turning into a passage that is formed into said traveling bracket to intersect an opening wherethrough one of the parallel rails is journaled.

6. A drill guide as recited in claim 1, wherein the trolley means is a rectangular block that is holed to accommodate the pair of spaced apart parallel rails journaled therethrough and includes a lateral passage that aligns with a straight wire or pin that is installed between said first and second guide cylinders; and the drill sleeve means includes external thread means for turning in a threaded end of said lateral passage.

7. A drill guide as recited in claim 6, wherein the trolley means includes means for locking to at least one of the parallel rails.

8. A drill guide as recited in claim 7, wherein the means for locking is at least one set screw means that is arranged for manual turning in a passage that is formed into said traveling bracket to intersect an opening wherethrough a rail is journaled.

9. A drill as recited in claim 6, wherein the drill sleeve means is removable.

* * * * *